United States Patent [19]

Cohen et al.

[11] Patent Number: 5,282,470

[45] Date of Patent: Feb. 1, 1994

[54] PROTECTIVE LENS COVER FOR A TONOMETER

[75] Inventors: Ben Z. Cohen, 140 E. 80th St., New York, N.Y. 10021; Mille Stand, Croton-on-Hudson; Laurabeth Fitzsimmons, Hastings-on-Hudson, both of N.Y.

[73] Assignee: Ben Z. Cohen, New York, N.Y.

[21] Appl. No.: 940,021

[22] Filed: Sep. 3, 1992

[51] Int. Cl.⁵ .............................................. A61B 3/16
[52] U.S. Cl. ................................................... 128/652
[58] Field of Search ............................ 128/645–652, 128/736; 604/263

[56] References Cited

U.S. PATENT DOCUMENTS

| | | | |
|---|---|---|---|
| 4,922,914 | 5/1990 | Segal et al. | 128/646 |
| 5,002,057 | 3/1991 | Brady | 128/652 |
| 5,031,622 | 7/1991 | Lahaye | 128/652 |
| 5,113,863 | 5/1992 | Herman | 128/652 |

*Primary Examiner*—Randy C. Shay
*Attorney, Agent, or Firm*—Anthony J. Casella; Gerald E. Hespos

[57] ABSTRACT

This invention provides an apparatus for covering the lens tip of a tonometer. The protective lens cover of the subject invention comprises a unitarily molded structure having an open end and an opposing closed end. The protective lens cover slidably receives onto the lens tip of a tonometer therein providing a temporary sterile environment to contact the eyeball of a patient.

8 Claims, 1 Drawing Sheet

PROTECTIVE LENS COVER FOR A TONOMETER

BACKGROUND OF THE INVENTION

The tonometer is an ophthalmologic apparatus used for detecting glaucoma. Glaucoma is a disease of the eye marked by increased pressure within the eyeball that can result in damage to the optic disk causing gradual loss of vision. Essentially, the tonometer is an instrument used to measure the tension of an eyeball. More particularly the tonometer accurately measures the intraocular pressure of the eyeball through the eye wall.

The tonometer functions such that the lens of a tonometer is positioned to contact an eyeball with a predetermined pressure. The eyeball is instantaneously deformed and the resistance of the eyeball to deformation is detected and measured as the intraocular pressure. There are two principal types of tonometers used in the ophthalmologic field at the present time, one being the pneumotonometer and the other being an applanation tonometer. The pneumotonometer detects eye pressure by means of a blast of air. Thus, the pneumotonometer does not require optics for viewing the deformed eyeball for the measurement of intraocular pressure. In contrast to the pneumotonometer, the applanation tonometer measures the intraocular pressure through measurement of the deformed surface area of the eyeball using optics. Although both of these tonometers use different methods to measure intraocular pressure, both still require its respective lens to come in contact with the eyeball of a patient.

Contact tonometers raise serious concerns regarding the spread of contagious disease. The possible spread of conjunctivitis, adenovirus, herpes simplex, and hepatitis between patients which come in contact with a common tonometer is of major concern. Additionally, the emergence of the epidemic AIDS only heightens this concern. Current methods for cleaning the tonometer lens tip include soaking the removable tip in cleansing chemical agents. Such chemical agents may include diluted bleach, hydrogen peroxide and isopropyl alcohol. Disadvantages with the use of these cleansing agents include incomplete tip disinfection, corneal contact with cleaning solutions, tonometer tip damage or loss, and the time and expense required for such cleansing.

One attempt to overcome the above mentioned disadvantages, is the Tonometer Probe Cap, manufactured by U.S. Optical Specialties, located in South Bend, Ind., and BioRad, Inc., located in Santa Ana, Calif. The Tonometer Probe Cap is designed to be used on the pneumotonometer. The tonometer probe cap is entirely constructed of latex. In use, the disposable Tonometer Probe Cap is placed over the tip of the pneumotonometer and provides a sterile environment devoid of contagious disease. Hence, every time the tip of the pneumotonometer is to contact a different patient, the attending physician places a new sterile latex probe cap over the tip of the pneumotonometer to ensure a sterile environment. However, the employment of the latex tonometer probe cap on the pneumotonometer may decrease the accuracy for the measurement of intraocular pressure of the eyeball. Additionally, the modern trend is to move away from the pneumotonometer for measuring intraocular pressure, as a blast of air on the eyeball is no longer looked favorable upon. Moreover, the latex tonometer probe cap is not applicable for usage on tonometers such as the applanation tonometer. The latter situation arises because tonometers such as the applanation tonometer measure the intraocular pressure through optics and, as mentioned above, the latex tonometer probe cap is designed to be employed on a nonoptical tonometer.

Accordingly, it is an object of the subject invention to provide a disposable sterile protective lens cover for an applanation tonometer.

Another object of the invention is to provide a protective lens cover for an applanation tonometer which greatly reduces the risk of the spread of contagious disease.

Still a further object of the subject invention is to provide a protective lens cover for a tonometer which enhances the optical qualities of the tonometer.

An additional object of the subject invention is to provide a protective lens cover which is packaged in a sterilized environment.

Yet another object of the subject invention is to provide a protective lens cover which is disposable after each patients usage.

It is another object of the subject invention to provide a protective lens cover that may be readily manufactured by a conventional molding process in quantities at a unit cost of pennies.

SUMMARY OF THE INVENTION

The subject invention is directed to a protective lens cover for an applanation tonometer, and is capable of preventing the spread of contagious disease arising from the multi-patient usage of a tonometer. The subject lens cover additionally provides optical enhancement for the lens of an applanation tonometer.

The subject protective lens cover is a unitarily molded structure and is preferably constructed of a clear polycarbonate plastic. The lens cover comprises a frustoconical structure having an open end and an opposing closed end, with the closed end being of the smaller diameter in contrast to the diameter of the open end. The protective lens cover further includes a conically grooved stepped portion along the inner surface intermediate the closed end and the open end. The conically grooved stepped portion enables detachment of the protective lens cover from a tonometer lens. The protective lens cover is typically dimensioned to conform with the outer dimensions of a tonometer lens so as to achieve a detachable interference fit between the two components.

The protective lens cover is sterilized and thereafter packaged in a sterilized environment. In use, the protective lens cover is removed from the sterilized packaged and is placed onto the lens of a tonometer so as to sustain a detachable interference fit such that the outer surface of the tonometer lens tip abuts against the inner surface closed end of the protective lens cover. Thereafter, the outer surface closed end of the protective lens cover is positioned to contact the eye wall of a patient such that the lens of the tonometer and the tonometer itself can accurately measure the intraocular pressure of the eyeball. After the tonometer testing procedure is complete, the protective lens cover is removed from the lens of the tonometer and permanently discarded. Thus, the lens of the tonometer never physically contacts the eyeball of a patient, as only the subject disposable sterile protective lens cover contacts the eyeball.

Additionally, the protective lens cover provides a more accurate measurement of intraocular pressure. As mentioned above, the protective lens cover is preferably constructed of a clear polycarbonate plastic, therein providing an excellent medium for the transductance of light waves. The protective lens cover improves the performance of the tonometer such that, after the protective lens cover is positioned onto the lens tip of the tonometer, the outer cylindrical wall of the protective lens cover functions to refract light waves from the immediate surrounding environment to the lens tip of the tonometer, whereupon the refracted light waves provide an improved enhanced view of the patient's eyeball.

More particularly, since the subject lens cover is packaged in a sterilized environment, the subject lens cover enables a tonometer to be used on numerous patients on a daily basis without the requirement of intricate cleansing procedures. After each patient is tested with the tonometer, a new sterilized protective lens cap is placed onto the lens tip of the tonometer while the previously used protective lens cap is permanently discarded. Therefore, the above mentioned cleansing procedures for the tonometer lens are no longer required. Moreover, the protective lens cover prevents the spread of contagious diseases and ensures a sterile environment for the lens tip of a tonometer. In summary, the subject invention provides an efficient and superior means in which to prevent the spread of contagious disease among the eyeballs of numerous patients while it provides improved performance for the tonometer.

DETAILED DESCRIPTION OF THE PREFERRED EMBODIMENT

Figure 1:
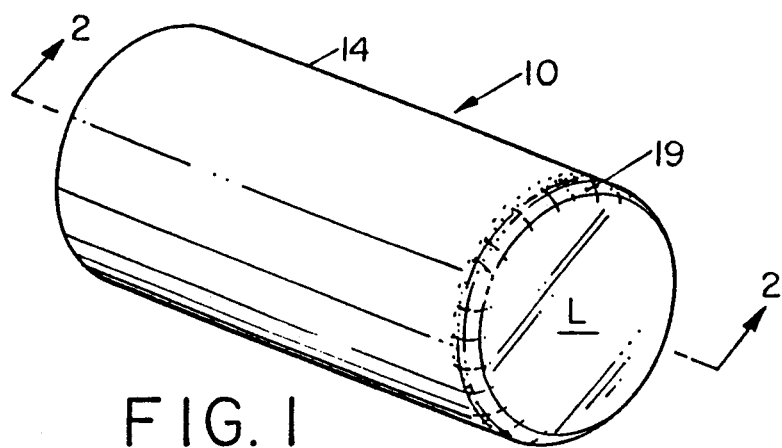
FIG. 1 is a perspective view of the protective lens cover of the subject invention.
Figure 2:
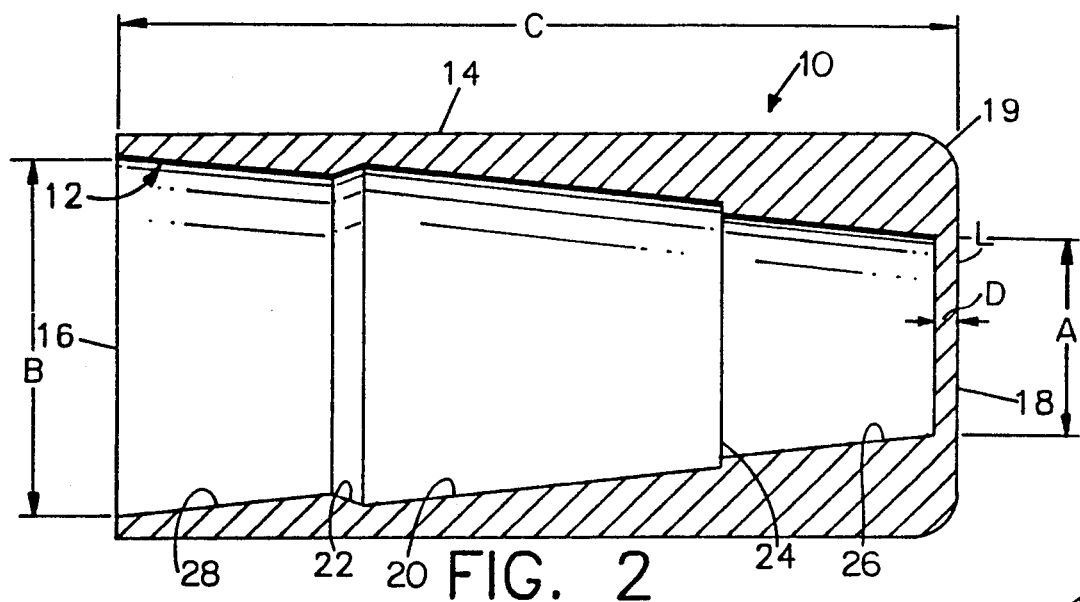
FIG. 2 is a cross-sectional view taken along line 2—2 of FIG. 1.

Referring to FIGS. 1 and 2, the protective lens cover of the subject invention is designated by the reference numeral 10. Protective lens cover 10 is a unitarily molded plastic structure and is preferably constructed of a clear polycarbonate plastic. The protective lens cover 10 comprises a cylindrical outer surface 14 and a stepped, frustoconical inner surface 12, with the protective lens cover 10 being open at end 16 and having an opposing planar closed end 18. The latter 18 intersects the cylindrical surface 14 of the lens cover 10 at an annular tapered edge 19.

The inner surface of planar closed end 18 is of smaller diameter "A", typically 0.312 inches, in contrast to the inner surface of open end 16, which typically has a diameter "B" of 0.435 inches. Generally, the overall length "C" of protective lens cover 10 is approximately 17/32 inches. Additionally, the planar closed end 18 of the protective lens cover 10 iS molded to form a clear Window or lens portion L having a uniform thickness "D" of approximately one thousandth of an inch. The protective lens cover 10 is typically dimensioned to slidably engage a standard tonometer lens so as to provide a sterilized protective lens cover for the lens.

The stepped inner surface 12 of the protective lens cover 10 includes a conically generated portion 26 adjacent the planar closed end 18, and a conically generated portion 28 adjacent the open end 16 of the protective lens cover 10. A conically grooved stepped portion 20 is disposed intermediate the portions 28 and 26. Stepped portion 20 includes an inclined transition portion 22 disposed between portions 20 and 28, and a right angle step 24 in the transition between portions 20 and 26. By this arrangement, the conically grooved stepped portion 20 effectively provides an undercut of the tapered inner surface 12 thereby facilitating radial expansion of the lens cover 10 at open end 16 as the lens cover 10 is slidably placed over the conical lens portion of a tonometer for fictionally engaging the same. It is particularly noted that, the configuration of the inner surface 12 of the protective lens cover 10 generally conforms to the outer configuration surface of the tonometer lens which may have a more generally cylindrical configuration in contrast to a conical configuration as illustrated in the drawings. As it may be readily appreciated, different manufactures of applanation tonometers design the latter to various configurations, some of which tend to have a more generally cylindrical configuration as opposed to a conical configuration.

Figure 3:
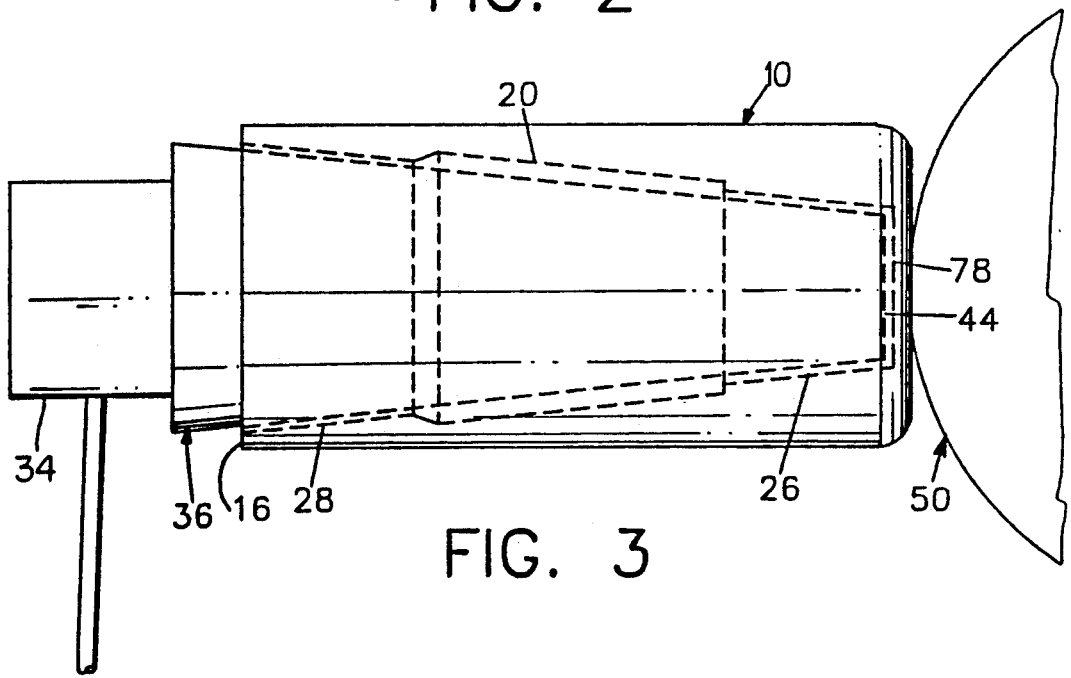
FIG. 3 is a side elevational view of the protective lens cover positioned on the lens housing of the tonometer as it contacts an eyeball.

In use, the protective lens cover 10 functions to provide a sterilized cover for the portion of the tonometer lens of an applanation tonometer which is intended to bear against the eyeball of a patient. As shown in FIG. 3, the tonometer includes a frustoconical lens 36 which typically is attached to a stem 34 which connects to the housing of a tonometer (not shown). The frustoconical lens 36 includes a clear, closed end lens tip 44. As shown in FIG. 3, the protective lens cover 10 is positioned on the lens 36 such that the closed end 18 of the cover 10 is placed over and abuts the tonometer lens tip 44. Additionally, the conically generated portion 26 and the conically generated portion 28 of the protective lens cover 10 engage the outer conical surface of the tonometer lens 36, such that the protective lens cover 10 is held in place by an interference fit with a tonometer lens 36. Thereafter, as shown in FIG. 3, the tonometer 36 and lens cover 10 are positioned to bear against the eyeball 50 of the patient, so as to enable the physician to take accurate measurements of the intraocular pressure of the patient's eyeball 50. After the intraocular pressure measurements are complete, the physician manually applies a radially inwardly directed force to the outer cylindrical surface 14 of the protective lens cover 10 in the proximate area of the conically grooved stepped portion 20. This radially inwardly directed force causes an inward deflection of the conically grooved stepped portion 20, thereby causing a slight radial outward expansion of the open end 16 of the lens cover 10, and thus relieving the interference fit force between the portion 28 of the lens cover 10 and the frustoconical surface of the tonometer lens 36. The relieving of the interference fit between the lens cover 10 and the tonometer lens 36 enables the physician to easily detract the protective lens cover 10 from the tonometer lens 36. Thereafter, the used protective lens cover 10 is permanently discarded and the above mentioned procedure to insert a new sterile protective lens cover 10 is repeated for the next application of the tonometer.

Although the invention has been described with respect to a preferred embodiment, it is apparent that modifications can be made without departing from the spirit and scope of the invention as defined by the appended claims.

We claim:

1. A protective lens cover for a tonometer lens of an applanation tonometer, comprising:

a unitarily molded structured made of clear plastic material and having an outer cylindrical surface, said structure being hollow to define an inner surface, said structure having a closed lens end and an opposed open end, the inner surface of said structure being frustoconical and including a conically grooved stepped portion disposed intermediate said open end and said closed end, said conically grooved stepped portion including an inclined portion in spaced relationship to the open end and a right angle stepped portion at a right angle to the outer cylindrical surface in the transition between said conically grooved stepped portion and the inner surface of the structure extending to said closed end, whereby said structure is radially expandable adjacent the open end thereof for achieving an interference interengagement with a tonometer lens, with the closed lens end of the structure being in abutment with the tonometer lens in order to provide a temporary sterile environment during an examination of a patient's eye.

2. A protective lens cover as in claim 1, wherein said unitarily molded structure is formed of a clear polycarbonate plastic.

3. A protective lens cover as in claim 1, wherein said closed lens end has a thickness of one thousandth of an inch.

4. A protective lens cover for the tonometer lens of an applanation tonometer, comprising:

a unitarily molded protective lens structure made of clear plastic material and having an outer cylindrical surface, said lens structure being hollow to define an inner surface having a closed lens end and an opposed open end, the inner surface of said protective lens structure being frustoconical, said inner surface further including a conically grooved stepped portion disposed intermediate said open end and said closed end, whereby said protective lens structure is dimensioned to be slidably receivable onto the tonometer lens so as to achieve friction fit with said tonometer lens, with the closed lens end of the protective lens structure being in abutment with the tonometer lens in order to provide a temporary sterile environment during an examination of a patient's eye.

5. A protective lens cover as in claim 4, wherein said unitarily molded structure is formed of a clear polycarbonate plastic.

6. A protective lens cover as in claim 4, wherein said closed lens end has a thickness of one thousandth of an inch.

7. A protective lens cover as in claim 4, wherein said conically grooved stepped portion includes an inclined portion in spaced relationship to the open end.

8. A protective lens cover as in claim 4, wherein said conically grooved stepped portion includes a right angle stepped portion at a right angle to the outer cylindrical surface in the transition between said conically grooved stepped portion and the inner surface of said protective lens structure extending to said closed end.

* * * * *